US010667717B2

(12) United States Patent  
Freeman et al.

(10) Patent No.: US 10,667,717 B2  
(45) Date of Patent: Jun. 2, 2020

(54) IMPEDANCE MEASURING DEVICES AND METHODS FOR EMERGENCY CARDIOVASCULAR CARE

(75) Inventors: Jenny E. Freeman, Weston, MA (US); Michael Lalli, Haverhill, MA (US); Anita Karcz, Watertown, MA (US); Alexander Panasyuk, Lexington, MA (US); Roman Bokhenik, North Easton, MA (US); Malcom G. Bock, Medfield, MA (US)

(73) Assignee: Respiratory Motion, Inc., Watertown, MA (US)

( * ) Notice: Subject to any disclaimer, the term of this patent is extended or adjusted under 35 U.S.C. 154(b) by 331 days.

(21) Appl. No.: 13/554,346

(22) Filed: Jul. 20, 2012

(65) Prior Publication Data

US 2013/0023781 A1    Jan. 24, 2013

Related U.S. Application Data

(60) Provisional application No. 61/509,952, filed on Jul. 20, 2011.

(51) Int. Cl.  
*A61B 5/053* (2006.01)  
*A61B 5/091* (2006.01)  
(Continued)

(52) U.S. Cl.  
CPC .......... *A61B 5/0535* (2013.01); *A61B 5/0809* (2013.01); *A61B 5/0816* (2013.01); (Continued)

(58) Field of Classification Search  
None  
See application file for complete search history.

(56) References Cited

U.S. PATENT DOCUMENTS 3,433,217 A    3/1969 Rieke  
3,690,143 A    9/1972 Day  
(Continued)

FOREIGN PATENT DOCUMENTS

EP    1302217    4/2003  
EP    2008581    12/2008  
(Continued)

OTHER PUBLICATIONS

EP Search Report for PCT/US2011/047812, dated Feb. 19, 2014.  
(Continued)

*Primary Examiner* — Michael R Bloch  
(74) *Attorney, Agent, or Firm* — Remenick PLLC

(57) ABSTRACT

Disclosed is a device, method and computer readable media for determining the adequacy of Cardiopulmonary Resuscitation (CPR). The device comprises an electrical source generator, an electrical signal sensor receiving a signal from the electrical source generator and a microprocessor. The microprocessor determines changes in impedance of the patient based on the signal received from the electrical signal sensor. Software executing on the microprocessor determines at least one of intrathoracic volume, change in intrathoracic volume, rate of compression, depth of compression, respiratory volume, and respiratory rate based on the change of impedance of the patient and outputs a signal indicating the adequacy of ventilation and compressions.

41 Claims, 4 Drawing Sheets

(51) Int. Cl.
  *A61N 1/39* (2006.01)
  *A61B 5/08* (2006.01)
  *A61H 31/00* (2006.01)
  *A61N 1/04* (2006.01)

(52) U.S. Cl.
  CPC .......... *A61B 5/091* (2013.01); *A61H 31/005* (2013.01); *A61N 1/3987* (2013.01); *A61B 2505/01* (2013.01); *A61H 2201/5012* (2013.01); *A61H 2201/5015* (2013.01); *A61H 2201/5048* (2013.01); *A61H 2201/5084* (2013.01); *A61H 2230/04* (2013.01); *A61H 2230/205* (2013.01); *A61H 2230/207* (2013.01); *A61H 2230/655* (2013.01); *A61N 1/046* (2013.01)

(56) References Cited

U.S. PATENT DOCUMENTS

| | | | |
|---|---|---|---|
| 3,742,936 | A | 7/1973 | Blanie |
| 4,036,217 | A | 7/1977 | Ito |
| 5,058,583 | A | 10/1991 | Geddes et al. |
| 5,469,859 | A | 11/1995 | Tsoglin et al. |
| 5,735,284 | A | 4/1998 | Tsoglin et al. |
| 5,953,441 | A | 9/1999 | Setlak |
| 6,168,568 | B1 | 1/2001 | Gavriely |
| 6,173,198 | B1 | 1/2001 | Schulze |
| 6,286,806 | B1 | 9/2001 | Cocoran |
| 6,366,803 | B1 | 4/2002 | Fee |
| 6,402,969 | B1 | 6/2002 | Calkins et al. |
| 6,809,462 | B2 | 10/2004 | Pelrine et al. |
| 6,976,963 | B2 | 12/2005 | Clift |
| 7,196,317 | B1 | 3/2007 | Meissner et al. |
| 7,361,146 | B1 | 4/2008 | Bharmi et al. |
| 7,530,956 | B2 | 5/2009 | Lewicke et al. |
| 8,096,962 | B2 | 1/2012 | Palazzolo |
| 8,306,611 | B2 | 11/2012 | Granov et al. |
| 2002/0032383 | A1* | 3/2002 | Weil et al. .................. 600/484 |
| 2004/0071337 | A1 | 4/2004 | Jeung et al. |
| 2004/0123667 | A1 | 7/2004 | McGrath |
| 2005/0033198 | A1 | 2/2005 | Kehyayan et al. |
| 2005/0090753 | A1 | 4/2005 | Goor et al. |
| 2005/0107719 | A1 | 5/2005 | Arad |
| 2005/0113702 | A1 | 5/2005 | Salla et al. |
| 2006/0058600 | A1 | 3/2006 | Eichler |
| 2006/0070623 | A1 | 4/2006 | Wilkinson |
| 2006/0241506 | A1 | 10/2006 | Melker et al. |
| 2006/0241513 | A1 | 10/2006 | Hatlestad |
| 2007/0010764 | A1 | 1/2007 | Palazzolo et al. |
| 2007/0060785 | A1* | 3/2007 | Freeman ................. A61H 31/00 600/16 |
| 2007/0276300 | A1* | 11/2007 | Olson et al. ................. 601/41 |
| 2008/0312565 | A1* | 12/2008 | Celik-Butler et al. .......... 601/43 |
| 2009/0062672 | A1 | 3/2009 | Sly et al. |
| 2009/0149748 | A1 | 6/2009 | Lenhardt et al. |
| 2009/0227849 | A1 | 9/2009 | Goor et al. |
| 2009/0264789 | A1* | 10/2009 | Molnar et al. ................. 600/544 |
| 2009/0264792 | A1 | 10/2009 | Mazar |
| 2009/0326253 | A1 | 12/2009 | Watson et al. |
| 2009/0326353 | A1 | 12/2009 | Watson |
| 2010/0049071 | A1 | 2/2010 | Goor et al. |
| 2010/0152600 | A1 | 6/2010 | Droitcour |
| 2010/0228166 | A1 | 9/2010 | Centen |
| 2010/0241181 | A1 | 9/2010 | Savage et al. |
| 2010/0312153 | A1* | 12/2010 | McIntyre et al. .............. 601/41 |
| 2011/0077497 | A1 | 3/2011 | Oster |
| 2011/0245712 | A1 | 10/2011 | Patterson et al. |
| 2011/0306850 | A1 | 12/2011 | Hatlestad et al. |
| 2012/0041279 | A1 | 2/2012 | Freeman |
| 2012/0165883 | A1 | 6/2012 | Kalgren et al. |
| 2013/0187941 | A1 | 7/2013 | Noon |
| 2013/0296823 | A1 | 11/2013 | Melker et al. |
| 2014/0073895 | A1 | 3/2014 | Brayanov |

FOREIGN PATENT DOCUMENTS

| | | |
|---|---|---|
| EP | 2018825 | 1/2009 |
| WO | WO00/33733 | 6/2000 |
| WO | WO 2006/006871 | 1/2006 |
| WO | WO2007/064682 | 6/2007 |
| WO | WO2007/147505 | 12/2007 |
| WO | WO 2008071439 A2 * | 6/2008 ............ A61B 5/053 |
| WO | WO2008/130549 | 10/2008 |
| WO | WO2009/035965 | 3/2009 |
| WO | WO2009/036312 | 3/2009 |

OTHER PUBLICATIONS

PCT Search Report for PCT/US2013/058797, dated Feb. 25, 2014.
PCT Search Report for PCT/US2012/47604, dated Oct. 12, 2012.
PCT Patentability Report for PCT/US2012/47604, dated Oct. 12, 2012.
EPO Search Report for PCT/US2011/047812, dated Feb. 19, 2014.
PCT Search Report for PCT/US2008/76224, dated Nov. 10, 2008.
PCT Patentability Report for PCT/US2008/76224, dated Nov. 10, 2008.
PCT Search Report for PCT/US2011/47812, dated Jan. 10, 2012.
PCT Patentability Report for PCT/US2011/47812, dated Jan. 10, 2012.
PCT Patentability Report for PCT/US2008/76224, dated Mar. 16, 2010.
EP Office Action for PCT/US2010/047604, dated Mar. 5, 2015.
EP Office Action for PCT/US2011/47812, dated Mar. 11, 2015.
Zulkarneev R Kh. Et al., A Hardware-Software System for Volumetric Calibration of Impedance Pneumograms, Biomedical Engineering, vol. 35, No. 1, 2001, pp. 48-51.
U.S. Appl. No. 13/210,360, filed Feb. 16, 2012, Freeman.
U.S. Appl. No. 13/554,346, filed Jan. 24, 2013, Freeman.
EP Office Action for Application No12815530.6, dated Apr. 13, 2016.
Pajic, et al, Model-driven safety analysis of closed-loop medical systems, IEEE Trans Industr Inform. vol. 10, pp. 1-35, p. 4, para. 1-2, Oct. 28, 2013.
CA Office Action for Application No. 2843806, dated Aug. 22, 2016.
Korea Office Action for Application No. 10-2014-7004400, dated Sep. 13, 2017.

* cited by examiner

IMPEDANCE MEASURING DEVICES AND METHODS FOR EMERGENCY CARDIOVASCULAR CARE

REFERENCE TO RELATED APPLICATIONS

The present application claims priority to Provisional U.S. Application No. 61/509,952, filed Jul. 20, 2011 and entitled "Use of Impedance Measurements for Measuring Intrathoracic Volume in Emergency Cardiovascular Care" which is incorporated in its entirety.

BACKGROUND OF THE INVENTION

Field of the Invention

This invention is directed to methods and devices for evaluating the adequacy of cardiopulmonary resuscitation and other emergency care. In particular, the invention is directed to instruments and methods that overcome deficiencies with current devices by using impedance signals to evaluate and optimize cardiopulmonary resuscitation and the administration of other emergency care.

Description of the Background

There is a need to evaluate the adequacy of cardiopulmonary resuscitation (CPR), whether by manual compression or automatic compression. Feedback to the operator during CPR is crucial as it improves the quality of CPR and greatly increases the patient's chances of survival. Currently, there are several devices and methods to monitor CPR from companies such as Philips, Laerdal, HeartSine, and Zoll. Progress has been made in CPR monitoring technology and the improvements in real world CPR performance have been documented by Philips and others. However, the devices currently on the market are inadequate to provide optimum ongoing feedback during CPR. It has been clearly shown that the quality of CPR has a direct effect on survival and overall patient outcome associated with cardiac arrest. Unfortunately, rescuers often do not perform CPR within established guidelines, whether they are lay persons or professionals. Frequently, compression rate, depth, recoil associated with complete release, consistent compression activity (versus "hands-off" time), and/or ventilation rate and depth are sub-optimal and negatively impact outcome. Inadequate compression rate and depth are common during CPR, resulting in inadequate movement of blood and oxygen. Too little compression does not provide adequate blood flow to maintain viability of the brain, heart, and other organs, and too much compression can cause rib fractures, cartilage separation, or coronary artery or cardiac conduction system damage. With increasing understanding of parameters of resuscitation associated with the best outcomes, it is important to evaluate and modify rescuer action to improve survival and optimize functional survival. Tools that can provide monitoring of the implementation of the various actions required for CPR can be used for developing CPR protocols, improving CPR training and providing real-time feedback in the clinical setting.

Basic Life Support (BLS) ventilation and chest compression skills are not always mastered or adequately retained by either laypeople or healthcare providers. Well-performed bystander CPR has been demonstrated to be a determining factor in survival from sudden cardiac arrest, but survival statistics remain low. Compliance with taught guidelines has been shown to be poor even immediately after CPR training courses. Studies have demonstrated that almost every kind of error, including overly rapid ventilation, inappropriately fast compressions, compressions with insufficient recoil and inappropriately shallow and slow compressions have been performed by hospital nursing staff. Notably, all the ways developed to measure CPR parameters in actual practice have deficiencies, and, in general, the quality of delivery of the various CPR parameters in actual practice is not really known.

To achieve effective CPR chest compressions, it is necessary to provide compressions at an appropriate rate and depth. The current American Heart Association (AHA) recommendation is to deliver compressions at a rate of 100 per minute. According to the 2010 AHA CPR guidelines, the recommended "compression-to-ventilation ratio [is] 30:2 for single rescuers of adults, children, and infants (excluding newly born infants)." This translates to only 3-4 breaths per minute and cycled with the compressions. The 2010 AHA Guidelines for CPR and Emergency Cardiovascular Care (ECC) continue to recommend that rescue breaths be given in approximately 1 second. Once an advanced airway is in place, chest compressions can be continuous (at a rate of at least 100/min) and no longer cycled with ventilations. Rescue breaths can then be provided at about 1 breath every 6 to 8 seconds (about 8 to 10 breaths per minute). Excessive ventilation should be avoided. A compression depth of at least 2 inches (5 cm) in adults and a compression depth of at least one-third (one-third to one-half) of the anterior-posterior diameter of the chest in infants and children (approximately 1.5 inches [4 cm] in infants and 2 inches [5 cm] in children) is recommended. Note that the range of 1.5 to 2 inches is no longer used for adults, and the absolute depth specified for children and infants is deeper than in previous versions of the AHA Guidelines for CPR and ECC. No specific tidal volume or minute ventilation parameters are recommended, since to date, until a patient is intubated and a ventilator is attached, it has not been possible to assess or track these parameters.

The 2010 guidelines recommend that "the adult sternum should be depressed at least 2 inches (5 cm)." This differs from the 2005 guidelines that stated "the adult sternum should be depressed approximately 1.5 to 2 inches (approximately 4 to 5 cm)." The underlying concept of CPR is that compressions create blood flow primarily by increasing intrathoracic pressure and directly compressing the heart. Compressions generate critical blood flow, oxygen, and delivery of other substances to the tissues, especially to the heart and brain. Unfortunately, rescuers often do not compress the chest adequately despite recommendations to "push hard." Often the important release (or recoil) phase is not well executed, and with incomplete recoil, the heart does not fill adequately in between compressions. The available science now suggests that compressions of at least 2 inches are more effective than compressions of 1.5 inches. For this reason, and to provide an easier message, the 2010 AHA Guidelines for CPR and ECC recommend a single minimum depth for compression of the adult chest. However, by simplifying the process, the chance of providing optimum care for a given individual (i.e. providing the most effective compressions without damaging the chest wall and intrathoracic structures) is reduced.

Significant effort has been undertaken to measure the quality of real world CPR and adherence to CPR guidelines. Two separate CPR studies have been conducted during actual resuscitations using a prototype defibrillator device with CPR quality measurement sensors. The prototype device used a Philips HeartStart 4000SP defibrillator with chest compression sensors designed by Laerdal. Laerdal and Philips Healthcare have incorporated measurement and feedback technology into a prototype HeartStart 4000SP defibrillator. The device includes a chest compression sensor with an accelerometer and a pressure sensor (designed by Laerdal) to measure compressions. The defibrillator has been modified to contain CPR quality analysis software which triggers CPR audio/visual feedback components. The HeartStart 4000SP was implemented in two separate studies to evaluate the quality of CPR in the real world. One study focused on out-of-hospital cardiac arrest and the other on in-hospital cardiac arrest. These studies provided objective data reporting the quality of CPR (as defined by international guidelines) delivered to actual resuscitation patients and found that CPR quality was inadequate in both in-hospital and out-of-hospital cases.

Philips reported an out-of-hospital study on 176 adult patients with cardiac arrest that examined the performance of paramedics and nurse anesthetists based on their adherence to international CPR guidelines. Ventilation rates were noted to be out of range a large majority of the time and higher than 20 ventilations/min over 60% of the time. Chest compressions were administered during only 48% of the time where no spontaneous circulation was documented. Only 28% of compressions were of appropriate depth. It is interesting to note that the paramedics and anesthesiology staff, who had had previous ACLS training with regular retraining, had all completed a refresher course immediately prior to study participation.

A second in-hospital study measured the quality of CPR parameters and assessed compliance to AHA and international guidelines in 67 resuscitations for cardiac arrest by well-trained basic life support (BLS) and advanced life support (ALS) staff. It was determined that: compressions were administered too slowly (<90/min) 28% of the time, over 37% of the compressions delivered were too shallow, and the mean percent of time without compressions while patients were in cardiac arrest was excessive (24%). The poor CPR quality of both in-hospital and out-of-hospital cardiac arrest cases suggests the need for CPR monitoring and CPR quality feedback to the operator.

Proper chest compressions are the most important factor regarding good-quality, successful CPR according to both human and animal studies, and even short 4- to 5-second interruptions in compressions decrease coronary perfusion pressure. Coronary perfusion pressure, or the difference between aortic pressure and right atrial pressure, is necessary to achieve return of spontaneous circulation. This means that interruptions to chest compression during CPR can adversely affect CPR performance. A Journal of the American Medical Association (JAMA) editorial addressed the quality of CPR and the need to update CPR and ECC guidelines, given the poor survival rates from cardiac arrest.

With the introduction of feedback protocols into CPR administration, improvements were noted. These have included the following: the percentage of compressions administered to the correct depth doubled, the average compression rate (which had tended to be too high) fell, and excessively high ventilation rates were reduced. In addition to supporting real-time CPR performance, it was demonstrated that a device that monitors and records CPR delivery can provide feedback that reinforces skills with every use, can provide data to demonstrate level of adherence to CPR guidelines and can illustrate areas for improvement. Protocols can be improved and such feedback can support research into the most critical factors in successful CPR and functional survival. Real time feedback can also contribute to resuscitation education in a variety of settings, including bystander, in-hospital and pre-hospital. Such feedback is discussed in U.S. Published Patent Application No. 2007/0010764, which is incorporated in its entirety herein.

Previous research at the Division of Air Medical Services at East Carolina University School of Medicine has demonstrated impairment of chest compression efficacy in the setting of an airborne BO-105 helicopter. This study was undertaken to determine whether in-flight compression efficacy could be improved with utilization of a pressure-sensing monitor providing real-time feedback during cardiopulmonary resuscitation (CPR). Ten flight nurses each performed two minutes of in-flight chest compressions on a mannequin that electronically assessed compression depth and hand placement. The session was then repeated with the addition of real-time feedback to the nurses from the pressure-sensing device. The mean proportion of correct compressions (95.7±3.2%) achieved with utilization of feedback from the pressure-sensing monitor was significantly higher ($P<0.01$) than the corresponding proportion for the control group (33.4±12.1%). This study demonstrated that the difficulties of performing effective in-flight chest compressions can be favorably impacted by adding real-time feedback on compression efficacy.

According to a report in Critical Care Medicine, EMS personnel tend to hyperventilate patients during out-of-hospital CPR. Artificial ventilations create positive pressure in the lungs and result in decreased coronary profusion pressure. As a result, less blood returns to the right side of the heart between compressions, reducing the effectiveness of CPR. A follow-up animal study showed that ventilation rates such as those found in the field cause reduced survival rates.

Researchers accompanied EMS personnel on calls and measured the number and duration of ventilations given during CPR. It was found that ventilations were given at an average rate of 37 per minute, whereas the recommended rate by the AHA was historically 12-15 breaths per minute and now is as low as 0 for non-ventilation CPR. As part of one training exercise, the EMS personnel were given training that specifically recommended lowering the number of ventilations. As a result, the number of ventilations decreased to 22 per minute, but the length of ventilations became longer, averaging 1.18 seconds instead of 0.85 seconds before training. Even after training, positive pressure in the lungs was reported to be present 47% of the time. In a related animal study, the researchers found that 6 out of 7 pigs survived when ventilation was performed at 12 breaths per minute and only 1 out of 7 pigs survived when ventilation was performed at 30 breaths per minute.

The researchers concluded that despite seemingly adequate training, professional rescuers consistently hyperventilate patients during out-of-hospital CPR. According to the study, individuals who perform CPR should monitor ventilation rates and limit them to no more than 12 breaths per minute. The report further suggests that these new findings should have significant implications for CPR research and the development of biomedical devices.

A device that accurately reports the adequacy of thoracic compressions and rescue breathing for a specific patient can greatly enhance both effectiveness and safety of CPR. A device that also instructs the caregiver how to improve and maintain optimal performance can be useful and potentially life-saving. Additionally, allowing complete recoil between compressions is particularly difficult for a caregiver or emergency rescuer to keep in mind, execute consistently and monitor effectively during CPR. A device that reports adequacy of recoil before the initiation of the next compression would be an advantage.

Sensors have been developed to measure CPR performance and algorithms have been developed to assess the difference or gap between CPR recommendations and the way it is actually performed and feedback has been delivered through visual, verbal or other auditory feedback. This type of feedback has been described previously and has the goal to have the following characteristics:

Provide correction when and only when compressions and/or ventilation deviates from recommended CPR guidelines. This can help caregivers and potential rescuers to remember and fine-tune their CPR skills during both training and during real-world CPR.

Provide clear, concise and easily interpretable data by visual or auditory means to optimize the capability of the caregiver or rescuer to react quickly.

Provide consistent, accurate and objective input from a specifically programmed device versus subjective information from another individual or sporadic data from another measurement device.

Provide real-time data so that the caregiver or rescuer can adjust their actions to optimize compressions and ventilation.

Provide prioritized input so that caregivers and rescuers can optimize overall CPR performance by making sure the most critical aspects of CPR are addressed first and fine-tuned as appropriate.

Existing Devices

Devices are available to assist rescuers to deliver compressions of appropriate rate and depth by visually and audibly indicating the rate and depth at which CPR chest compressions should be performed. The CPR devices currently available use methods such as metronomes, pressure pads, accelerometers, and transthoracic impedance measurements as their underlying technology to monitor the quality of CPR and communicate recommendations. All these CPR monitoring methods have deficiencies that can lead to poor CPR performance, which are overcome by the invention described in this patent. Patents have also been issued for devices that perform CPR mechanically.

Audio feedback has been demonstrated to improve CPR performance. Some devices deliver an audible tone at a constant rate of 100 tones per minute and/or visual flashes at the appropriate rate to indicate how often the chest needs to be compressed for optimal CPR. This metronome method helps the rescuers time compressions, but does not report if the compressions are at the advised rate and depth.

Several patents have been granted for devices that mechanically compress a patient's chest but these methods have not been shown to be an improvement over manual CPR. The 2010 AHA guidelines report that "at the time of the 2010 International Consensus Conference there were still insufficient data to demonstrate that any drugs or mechanical CPR devices improve long-term outcome after cardiac arrest. Clearly further studies, adequately powered to detect clinically important outcome differences with these interventions, are needed." To date, attempts at tailoring mechanical CPR to individuals to improve outcomes has not been accomplished and mechanical CPR is still not included in the guidelines. One of the drawbacks of current mechanical CPR is that there is not adequate feedback of changes in intrathoracic volumes to optimize its implementation. Therefore, an integrated device that can provide ongoing audio feedback for both compression rate and depth as well as adequacy of ventilation preferably optimizes CPR performance.

One device, the ZOLL's CPR-D-padz, utilizes an accelerometer incorporated into a pad placed on the sternum. The system converts the motion of the accelerometer over time into distance moved during each compression, providing a real time assessment of the rate and depth of compressions. The device shows CPR compression depth on the display screen. It also provides an adaptive metronome to help the rescuer with the proper rate and depth and will make recommendations, i.e. saying "Push harder" or "Good compressions," as needed. This device relies on the movement of the accelerometer to provide a measurement of the depth of each compression, which is recommended to be greater than 2 inches by the 2010 guidelines. Optimum compressions will vary depending on the patient's build and anatomy, but the guidelines are simplified because most CPR is carried out without such feedback. For instance, some experts in the field recommend 3 inches for larger men.

Another product on the market, the Philips Q-CPR, provides a real-time CPR measurement and feedback tool to provide objective measurement and real-time corrective feedback on both the compression and ventilation components of CPR. This feature is available in both manual defibrillation and AED modes. This device derives information about compression depth and rate via an accelerometer and pressure sensors, but also uses intrathoracic impedance measured through the defibrillation pads to calculate ventilation rate in order to provide additional data to encourage caregivers to perform CPR on adults in accordance with AHA/ILCOR guidelines. Of note, the Philips Q-CPR does not use thoracic impedance measurements to measure or deliver information related to intrathoracic or lung volumes, but only to report rate of ventilation, which is presented as ventilations-per-minute (vpm). These systems do not have the capability to measure intrathoracic volumes or intrathoracic volume changes associated with cardiac compressions and/or ventilator volumes.

There are several specific disadvantages to the Philips Q-CPR device, the Zoll CPR-D padz, and other devices which rely solely on an accelerometer to determine the proper depth of compression. Small errors in measured acceleration can lead to unacceptably large errors in reported chest displacement. It has been shown that an error in measured acceleration as small as 0.02 in/sec$^2$ leads to a displacement error of 0.25 inches. An error in displacement is a problem since while the AHA guidelines specify that the chest must be compressed at least 2 inches, a significantly larger compression, for example, in a small woman could lead to significant damage to ribs. Even the recommended 2 inches of compression could be too much for an elderly frail woman with osteoporosis.

Additionally, current devices are prone to external acceleration error and errors due to drift from the initial starting position. Acceleration errors, caused by accelerations other than the application of CPR, can occur because the accelerometer cannot determine where the acceleration originated. Therefore, if a patient is being transported in an ambulance, the accelerometer could measure vibrations and bumps in the road and produce displacement errors. As a result, the operator could be instructed to perform CPR with inaccurate timing and compression depth.

Another possible cause of error in accelerometer based devices is drift from the actual, or reported starting position of the accelerometer. The accelerometer is used to calculate displacement from the starting position, which is on top of the chest before a compression. After the first compression, the accelerometer only detects a relative location for the starting point, not an exact initial starting location. As repeated compressions are applied, the reported displacement may drift since the accelerometer has no "memory" of the initial starting position.

Drift can occur, for example, if the chest is not allowed to return to a fully relaxed position between compressions. The accelerometer could begin to use the new, lower, starting position as if it was the original starting position. As a result, the device would instruct the operator to compress the chest harder and deeper than necessary and potentially break the patient's ribs. Drift can also occur due to a gradual slip of the accelerometer on the body or if ventilation is performed simultaneously with CPR.

Even if properly operated under ideal conditions, drift still occurs with accelerometer based CPR devices. If a rib breaks during CPR, the chest will gradually change shape and cause the accelerometer's starting position to drift. Other types of injury or disease can also cause the chest to gradually change shape. Also, because the electrodes and accelerometer are a single entity in such devices, placement is compromised. Anterior-posterior and apex-sternum are not afforded to the CPR operator. Thus, pediatric use for such devices is not viable. A CPR device should be able to instruct the operator to perform CPR with the correct frequency and depth of compression without erroneous drift and without being affected by external accelerations, which is not possible with current accelerometer based CPR devices.

One product, known as the ResQPOD developed by Advanced Circulatory Systems, Inc., is a one-way valve attached to a face mask or an endotracheal tube and is used with a ventilation bag. It essentially blocks air from entering the lungs during the decompression phase of CPR, thereby creating a vacuum in the lungs. The vacuum creates suction, which draws more deoxygenated blood back from the veins of the arms and legs, which, in turn, allows for more blood flow going out, especially to the brain.

One product, on the market (Q-CPR by Philips), provides a real-time CPR measurement and feedback tool to provide objective measurement and real-time corrective feedback on both the compression and ventilation components of CPR. This product is available in both manual defibrillation and automated external defibrillator (AED) modes to provide information about compression depth and rate as well as ventilation rate to encourage caregivers to perform CPR on adults in accordance with AHA/International Liaison Committee on Resuscitation (ILCOR) guidelines.

Another Philips device in the marketplace utilizes multi-function pads placed on the patient's chest with the CPR meter applied to the center of the patient's chest. During use, the CPR meter measures chest compression depth and rate while a ventilation algorithm analyzes chest impedance measured from the multifunction pads to produce a ventilation rate. An anterior/anterior pads placement is required because the algorithm interprets change in impedance based on thorax/sternum placement. The compression and ventilation algorithms produce visual measurements and related auditory/textual feedback, as appropriate, through a feedback algorithm.

In the Philips device, compression depth is presented as a waveform that represents about 10 seconds of compressions, as derived from signals from the CPR meter. As the chest is compressed, the compression is represented as a downward stroke of the wave, rebounding up to a baseline as compression pressure is released. Two horizontal lines in the wave sector drawn at −38 mm and −51 mm (−1.5" and −2") indicating the target zone to help achieve good compression depth. A calculated compressions-per-minute (cpm) rate is displayed. If compression depth or rate deviates significantly from AHA/ILCOR guidelines, the monitor/defibrillator provides visual and corrective audible feedback. If there are no detectable compressions, a No Flow time value will count "hands off" seconds, starting at 2 seconds and increment with each additional second.

The defibrillation pads collect ventilation data by detecting changes in thoracic impedance. The ventilation rate is presented as ventilations-per-minute (vpm) Like compression, if the ventilation rate falls outside the AHA/ILCOR guidelines, visual and audible feedback is given.

Audible voice prompts (in manual and automated external defibrillator (AED) modes) and on-screen text prompts (in AED mode—Basic View only) alert the caregiver to needed adjustments in CPR performance, including a lapse in compression activity. Feedback is prioritized and delivered in the order of clinical importance. The feedback is also tiered so the caregiver receives visual feedback first and then a voice prompt only if a correction is not made based on the initial visual prompts. LED pressure sensors exist to assist the operator to provide consistent chest compression. One such device, (CPREzy Pad, CPREzy, Herfordshire, UK) is designed so that when pressure is applied by hand to a pad, pressure sensitive light emitting diodes indicate the correct amount of force required for each chest compression. Four green LED's are present on the device to indicate the target pressure required for patients of different weight and size. Rescuers need to estimate the size of the patient and apply sufficient pressure to illuminate the corresponding LED. A yellow light can alert the rescuer that too great a pressure is being applied. The rescuer achieves this risk reduction by applying only enough force to illuminate the LED that corresponds to the victim's approximate size. Rescuers also need to be aware of an increased risk of chest injury when the caution light is illuminated during compressions. Furthermore, such a device is cumbersome and not easily implemented in the CPR setting.

Another device designed to help assess the quality of CPR is the HeartSine Samaritain PAD500P with built in defibrillator. The Samaritan PAD500P uses an Impedance Cardiogram (ICG) to assess how well the CPR is being preformed. The ICG waveform represents the cardiac output, and can be used to detect blood flow through the aorta and the pulmonary vessels. ICG signals are examined by a diagnostic algorithm in the microprocessor and are used to provide the operator with compression depth feedback. The device also measures the ECG, which is used to analyze when an electric shock from the defibrillator should be delivered.

To obtain the ICG waveform, transthoracic impedance is measured using electrodes. Respiratory influences from the transthoracic impedance measurements are deliberately filtered out to obtain the ICG. Therefore the PAD500P only measures the cardiac output and cannot be used to measure ventilation volume or respiratory rate.

Impedance cardiography is inherently inaccurate during CPR due to the influence of natural catecholamines or injected epinephrine which constrict blood vessels and alter the way that blood flows through the chest. Patients with an abnormal state of hydration pose an additional problem to impedance cardiography by changing the baseline impedance, which is why it is important to combine impedance cardiography with impedance pneumography.

Measuring intrathoracic volume, tidal volume and minute volume are useful for optimizing CPR. Depending on the circumstances, CPR may or may not include rescue breathing. In cases in which CPR does not include rescue breathing, it is even more imperative to record the volume of air moving into and out of the lungs during compressions. In cases in which rescue breathing is administrated, either by mouth to mouth resuscitation or through a breathing tube, rescue breathing should be optimized for the patient. Rescue breathing at a high rate and high volume can cause damage to the lungs and decrease the efficacy of chest compressions by increasing the intrathoracic pressure. The best way to administer rescue breathing or ventilation during CPR is with a rate of 8 to 10 ventilations per minute. This balances the priority of having a low mean intrathoracic pressure with the priority of oxygenating the patient. A low mean intrathoracic pressure allows the heart to more easily pump blood into the surrounding vasculature. Monitoring the volume of inhaled air and providing feedback to CPR technicians or ventilation units can ensure that the administration of CPR fits the guidelines of the AHA or ERC, and that rescue breathing is optimized to maximize patient survival rates.

After defibrillation and CPR are administered and the heart recovers enough to start pumping on its own, it is important to ensure that pumping requires as little energy as possible. When the intrathoracic pressure is low, the heart can pump blood into the surrounding tissue with less energy. The key to maintaining a low intrathoracic pressure is by controlling breathing by lowering respiration rate while maintaining constant minute ventilation. This ensures that enough air is being respired, while maintaining a low mean intrathoracic pressure, allowing the heart to recover.

While attempting to measure cardiac activity, Atzler and Lehmann noted transthoracic electrical impedance changed with respiration. They regarded the respiratory impedance changes as artifacts and asked the patients to stop breathing while measurements were made. In 1940, while also studying cardiac impedance, Nyboer noticed the same respiratory impedance artifact in his measurement. He confirmed the origin of the artifact by being the first person to relate changes in transthoracic impedance to changes in volume using a spirometer by simultaneously recording both. Goldensohn and Zablow took impedance pneumography a step further by being the first investigators to quantitatively relate respired volume and transthoracic impedance. They reported difficulty in separating the cardiac signal artifacts and also noted artifacts during body movements. After comparing the impedance changes and respired volume changes by a least squares regression, they determined that the two are linearly related. Other groups have confirmed the linear relationship between transthoracic impedance changes and respiratory breaths and found that approximately 90% of the spirometric signal can be explained by the thoracic impedance signal. While the relationship has been shown to be linear, many groups found the calibration constants for intrapatient and interpatient to be highly variable between trials. These differences in calibration constants can be attributed to a variety of physiological and electrode characteristics, which must be taken into account.

SUMMARY OF THE INVENTION

The present invention overcomes problems associated with current strategies and designs and provides new systems and methods of monitoring patients. Current CPR monitoring methods and devices have deficiencies that can lead to poor CPR performance. The device and methods of the present invention overcome the deficiencies described herein. The present invention also overcomes significant disadvantages associated with metronome based, accelerometer based, and other forms of transthoracic impedance based devices.

In the present invention, unlike the constant 100 compression per minute provided by metronome devices, feedback is given based on CPR performance. The feedback can advise an operator to compress faster or slower. Also unlike metronome devices, the present invention can advise the operator on the depth of chest compression and can indicate ventilatory parameters.

Unlike accelerometer based devices (e.g. from Philips and Zoll), the present invention is not affected by drift or external accelerations during CPR monitoring. This allows for accurate CPR feedback in moving vehicles. The present invention also allows the operator to compress the patient's chest with proper depth even if the operator applies some force to the chest between compressions. This occurs often during CPR and would cause drift errors with accelerometer based devices.

Unlike the HeartSine PAD500P, the present invention utilizes impedance recordings to report effects of chest compressions on intrathoracic volumes and can be used to optimize both rescue breathing and chest compressions. Thoracic impedance measurements can be used to determine the tidal volume, rate, and minute volume of rescue breathing. Audible and visual feedback regarding rescue breathing helps prevent hyperventilation during CPR, which is known to cause detrimental patient outcomes.

One embodiment of the invention is directed to a device for determining the adequacy of Cardiopulmonary Resuscitation (CPR). The device comprises an electrical current source generator, an electrical voltage sensor sensing the current generated by the electrical current source generator, a microprocessor, wherein the microprocessor determines changes in impedance of the patient based on the current sensed by the electrical voltage sensor, and software executing on the microprocessor. The software determines at least one of intrathoracic volume, change in intrathoracic volume, rate of compression, depth of compression, respiratory volume, and respiratory rate based on the change of impedance of the patient, and outputs a signal indicating the adequacy of at least one of ventilation and compressions.

In the preferred embodiment, the current source generator is comprised of at least one of a function generator, a current generator, and a current monitor. Preferably, the electrical voltage sensor comprises at least one of an input amplifier, a signal filter, an analog divider, a rectifier, a root mean square to direct current (RMS-to-DC) chip, a band-pass filter, a multiplexor, and an output amplifier. Preferably the device comprises two demodulators and the first demodulator filters a signal with a generator signal as a carrier and the second demodulator filters the signal with 90-degree phase rotating circuitry.

Preferably, the electrical source generator, the electrical voltage sensor, and microprocessor are fully integrated into a lead impedance electrode pad. Preferably the device further comprises at least one of ventilator, an automatic compression device, and a defibrillator. The signal is preferably a closed feedback that directs at least one of the ventilator, the automatic compression device, and the defibrillator to adjust at least one of compression rate, depth of compression, complete release, no compression activity, and ventilation rate. Preferably, the device directs the timing of defibrillation.

In the preferred embodiment, the device further comprises leads coupling the patient to the electrical source generator and the electrical signal sensor. The leads are preferably coupled to paddles of the defibrillator. Preferably, the device is electronically protected from a shock generated by the defibrillator Another embodiment of the invention is directed to a method of determining the adequacy of Cardiopulmonary Resuscitation (CPR). The method comprises generating an electrical current at an electrical current generator, passing the electrical current through a patient, receiving the current at an electrical voltage sensor after the current passed through the patient, measuring changes in impedance levels of the patient at one or multiple frequencies, determining at least one of intrathoracic volume, change in intrathoracic volume, rate of compression, depth of compression, respiratory volume, and respiratory rate based on the change of impedance of the patient, and outputting a signal indicating the adequacy of at least one of ventilation and compressions.

Preferably, the electrical source generator is comprised of at least one of a function generator, a current generator, and a current monitor. The electrical voltage sensor preferably comprises at least one of an input amplifier, a signal filter, an analog divider, a rectifier, a root mean square to direct current (RMS-to-DC) chip, a band-pass filter, a multiplexor, and an output amplifier. The method preferably further comprises directing the timing of defibrillation. Wherein the method is executed on a device comprising two demodulators and the first demodulator filters a signal with a generator signal as a carrier and the second demodulator filters the signal with 90-degree phase rotating circuitry.

Preferably, the method further comprises at least one of ventilator, an automatic compression device, and a defibrillator. In the preferred embodiment, the signal is a closed feedback that directs at least one of the ventilator, the automatic compression device, and the defibrillator to adjust at least one of compression rate, depth of compression, complete release, no compression activity, and ventilation rate. The output signal preferably indicates adequacy of ventilation is visible ore heard from the lead or impedance electrode pad.

The method preferably comprises coupling leads to the patient, the electrical current generator, and the electrical voltage sensor. The method preferably comprises coupling the leads to paddles of the defibrillator. The device is preferably electronically protected from shock generated by the defibrillator Another embodiment of the invention is directed to a computer-readable media containing program instructs for determining the adequacy of Cardiopulmonary Resuscitation (CPR), that causes a computer to generate an electrical current at an electrical current generator, inject the electrical signal into a patient, receive the current at an electrical voltage sensor after the current passes through the patient, measure change in the impedance level of the patient, determine at least one of intrathoracic volume, change in intrathoracic volume, rate of compression, depth of compression, respiratory volume, and respiratory rate based on the change of impedance of the patient, and output a signal indicating the adequacy of ventilation and compressions.

Preferably, the electrical current generator is comprised of at least one of a function generator, a current generator, and a current monitor. In the preferred embodiment, the electrical voltage sensor comprises at least one of an input amplifier, a signal filter, an analog divider, a rectifier, a root mean square to direct current (RMS-to-DC) chip, a band-pass filter, a multiplexor, and an output amplifier. Preferably the computer is coupled to two demodulators, wherein the media further causes the computer to filter a signal with a generator signal as a carrier through the first demodulator and to filter the signal with 90-degree phase rotating circuitry through the second demodulator. Preferably the computer is coupled to at least one of ventilator, an automatic compression device, and a defibrillator. Preferably, the media further directs at least one of the ventilator, the automatic compression device, and the defibrillator to adjust at least one of compression rate, depth of compression, complete release, no compression activity, and ventilation rate.

Another embodiment of the invention is directed to a cardiopulmonary resuscitation (CPR) intrathoracic volume indicator. The CPR intrathoracic volume indicator comprises an impedance monitoring device coupled to a patient, an impedance processing device in communication with the impedance monitoring device, wherein the impedance monitoring device determines if the impedance falls outside a predetermined impedance range, and an indicator to alert a CPR giver of impedance outside of the predetermined impedance rage.

In the preferred embodiment, the impedance processing device determines at least one of intrathoracic volume, change in intrathoracic volume, rate of compression, depth of compression, respiratory volume, and respiratory rate based on the change of impedance of the patient. Preferably, the indicator is at least one of an audio and a visual indicator. Preferably the indicator is coupled to an automated external defibrillator, the defibrillator comprising patient electrodes that apply a shock to the patient and obtain the impedance from the patient. The device is preferably integrated into a lead impedance electrode pad.

Other embodiments and advantages of the invention are set forth in part in the description, which follows, and in part, may be obvious from this description, or may be learned from the practice of the invention.

DESCRIPTION OF THE INVENTION

Figure 1:
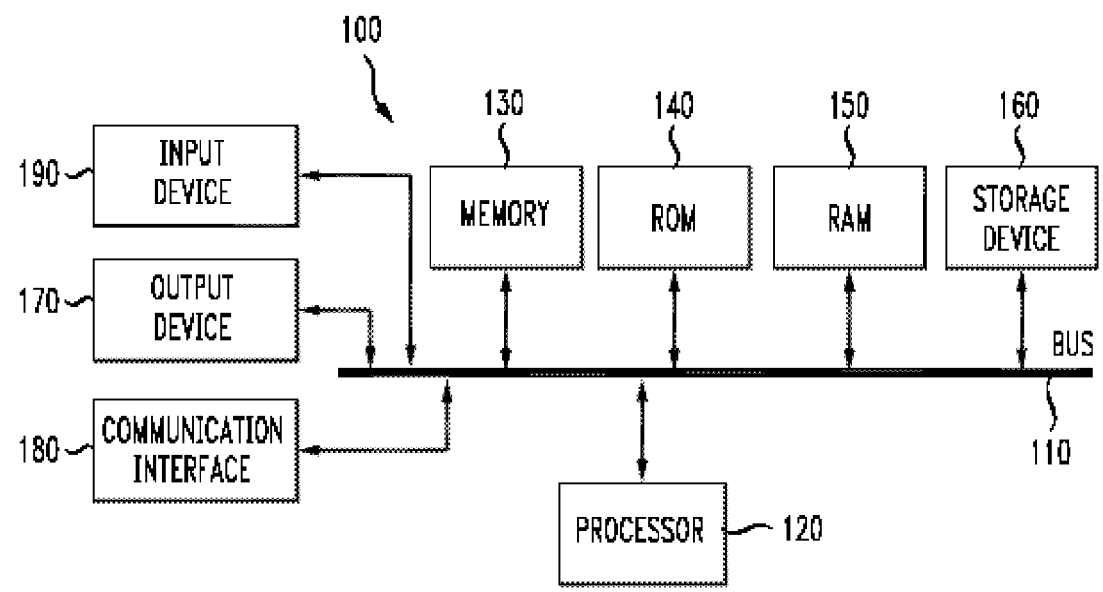
FIG. 1 illustrates one embodiment of a system of the invention.

As embodied and broadly described herein, the disclosures herein provide detailed embodiments of the invention. However, the disclosed embodiments are merely exemplary of the invention that may be embodied in various and alternative forms. Therefore, there is no intent that specific structural and functional details should be limiting, but rather the intention is that they provide a basis for the claims and as a representative basis for teaching one skilled in the art to variously employ the present invention.

It has surprisingly been discovered that the measurement of thoracic impedance is a simple method that can yield intermittent readings or continuous tracings related to intrathoracic volume without requiring an invasive catheter, without requiring cumbersome devices to be placed on the thorax, without impeding airflow, without restricting body movements, without the requirement for a device to be inserted at the site where CPR is being delivered, and without restricting access to the chest and airway to perform CPR.

Impedance is represented as a complex quantity (z) and the term complex impedance may be used interchangeably; the polar form conveniently captures both magnitude and phase characteristics, $z=|z|e^{j\theta}$, where the magnitude $|z|$ represents the ratio of the voltage difference amplitude to the current amplitude, while the argument $\theta$ gives the phase difference between voltage and current. j is the imaginary unit, and is used instead of i in this context to avoid confusion with the symbol for electric current. In Cartesian form, $z=R+jX$, where the real part of impedance is the resistance R and the imaginary part is the reactance x.

Impedance is used as the measurement of opposition to an alternating current. Mathematically, impedance is measured by the following equation, which is analogous to Ohm's law:

$$Z=V/I \quad (1)$$

where, voltage=V, current=I, and impedance=Z. An object that conducts electricity with unknown impedance can be determined from a simple circuit. Applying a known alternating current across an object while simultaneously measuring the voltage across the object and using equation (1) yields the impedance. The thorax represents a volume conductor, and because of that, the laws governing ionic conductors can be applied. In addition, the movement of organs and the enlargement of the thoracic cage during breathing or compressions create a change in conductivity, which can be measured. Impedance across the thorax is measured by introducing a known current and measuring the change in voltage across the thorax with electrodes.

The tissue layers that make up the thorax and the abdomen all influence the measurement of transthoracic impedance. Each tissue has a different conductivity that influences the magnitude and direction of current flow between electrodes. Beginning with the outermost layer, the surface of the body is covered by skin, which presents a high resistivity but is only about 1 mm thick. Under the skin is a layer of fat, which also has a high resistivity. However, the thickness of this layer is highly variable and depends on body location and the body type of the subject. Moving posterior to anterior, below the layer of skin and fat, are the postural muscles, which are anisotropic. They have a low resistivity in the longitudinal direction but a high resistivity in all other directions, which leads to a tendency to conduct current in a direction that is parallel to the skin. Below the muscle are the ribs, which, as bone, are highly insulating. Therefore, current through the thorax can only flow between bones. Once current reaches the lungs, it is hypothesized that current travels through the blood, which has one of the lowest resistances of any body tissue. Aeration of the lungs and compression of the chest changes the size of the lung and the pathway of current flow, and manifests itself as a change in resistance or impedance that can be measured.

Due to the anisotropic properties of the tissues, radial current flow through the chest is much less than would be expected. Much of the current goes around the chest rather than through it. As a result, impedance changes come from changes in thoracic circumference, changes in lung size, and movement of the diaphragm-liver mass. Measurements at lower thoracic levels are attributed to movement of the diaphragm and liver, and at higher thoracic levels the measurements are attributed to aeration and expansion of the lungs. Under normal circumstances and during CPR, impedance measurements reflect both expulsion of air from the lungs, as associated with compressions, and ventilation of the lungs by natural and artificial means, including air entry associated with CPR itself, mouth-to-mouth, mask ventilation, bag ventilation of an end tracheal tube, or mechanical ventilation. Under any circumstance, analysis of the impedance signal reflects intrathoracic volume. This can be analyzed and algorithms developed and used to deliver information as to total thoracic volume which reflects both ventilation and circulation during CPR and, in addition, to separate out and quantify ventilation and separate out and quantify circulation. This can be performed by analyzing the total signal or by combining data from Respiratory Variation Monitoring (RVM) regarding lung volumes and rate and Impedance Cardiography (ICG) pertinent to circulatory physiology. ICG alone is insufficient to report changes associated with CPR due to the effects of cardiac compression on intrathoracic volumes and due to endogenous or exogenous catecholamines and administration of other drugs or intravenous fluids. In one embodiment, the invention delivers information related to overall impedance changes during CPR, without filtering, which focuses on hemodynamic information and the status of blood or fluid in the tissue. In another embodiment, the invention delivers information only related to changes in impedance related to the expulsion of air from the chest during compressions. In another embodiment, information about hemodynamics within the impedance signal, similar or identical to ICG, can be added to RVM measurements to deliver information to the caregiver regarding adequacy of compression, adequacy of ventilation, or adequacy of the CPR in general. In the situation of CPR, the impedance signal is the sum of the change from the expansion and aeration of the lungs and compression of the chest cavity and the movement of the diaphragm-liver mass. Given evidence that the timing of defibrillation relative to the state of the filling of the heart based on either intrinsic cardiac action or chest compressions, in one embodiment, defibrillation is coordinated with the timing of chest compression to optimize results. In one embodiment, defibrillation is recommended, by voice or other signal, or automatically delivered at a time determined by impedance measurements that reflect automatic or rescuer delivered chest compression and mechanical or bag ventilation.

CPR

It has surprisingly been discovered that impedance measurements can reflect total intrathoracic volume which relates to lung volume and cardiac volume in the CPR situation. CPR works by compressing the thorax and forcing blood out of the heart to the brain and body. Each compression in the non-intubated patient both pushes blood out of the heart and air out of the lungs. In this case, the measured impedance decreases. This is precisely when and how blood is pumped to the body, brain and heart during CPR. During resuscitation breathing by mouth to mouth or mask ventilation in the non-intubated patient, or during bag ventilation (or mechanical ventilation) in the intubated patient, air is pushed into the lungs and thorax. When the intrathoracic pressure is elevated and the lungs are expanded during ventilation, the impedance goes up. Increases in intrathoracic pressure associated with ventilation can be either synergistic or competitive with cardiac compressions to force blood out of the heart to supply the body. Monitoring changes in impedance can optimize effectiveness of cardiac compressions. The invention can collect and analyze data and provide feedback to caregivers to optimize delivery of CPR based on impedance that takes both compressions and ventilations into account.

Timing

Given evidence that the timing of defibrillation relative to the state of the filling of the heart based on either intrinsic cardiac action or chest compressions, in one embodiment, defibrillation is coordinated with the timing of chest compression to optimize results. In one embodiment, defibrillation is recommended, by voice or other signal, or automatically delivered at a time determined by impedance measurements that reflect automatic or rescuer delivered chest compression and mechanical or bag ventilation.

Influences of Electrode Placement

For a given change in volume, laying supine yields the greatest signal amplitude and lowest signal to noise during respiration. All CPR patients are preferably supine.

One embodiment of the invention provides absolute measurements of thoracic impedance; another embodiment of the invention provides a trend in thoracic impedance. Either an absolute measurement of intrathoracic volume or a trend could be useful to CPR providers.

Despite having the same electrode placements, calibration constants and signal amplitudes for individuals of different sizes showed variability. Changes in impedance for a given change in volume are generally the largest for thin-chested people and smaller for people who are more amply sized. These observed differences are due to the greater amount of resistive tissue, such as adipose tissue and muscle, between the electrodes and lungs in larger subjects, yielding an overall smaller percent change in impedance for a given change in volume for larger subjects. On the other hand, in children the cardiac component of the impedance trace is generally greater than in adults. This is due to greater fat deposition around the heart in adults than in children, which serves to shield the heart from being incorporated into the impedance measurement.

In experiments, electrodes attached to the mid-axillary line at the level of the sixth rib yielded an accurate way of measuring impedance change during respiration. Greater linearity between the two variables was attained by placing the electrodes higher on the thorax. Variability in impedance measurements is comparable to those seen in measurements of other vital signs, such as blood pressure. Thoracic impedance measurements are sufficiently accurate for clinical purposes. Digital signal processing allows for the near instantaneous filtering and smoothing of real-time impedance measurements, which allows for the minimization of artifacts and noise. Thoracic impedance is used in long-term patient monitoring. As long as the electrodes remain relatively unmoved, the relationship of change in impedance to change in volume is stable for long periods of time. This information can be used as the patient is weaned off CPR to ensure adequacy of ventilation and circulation.

In one embodiment, the change in impedance or δI can be used to calculate the compression volume. There are two major influences on the impedance curve. The first one is the flow of blood to and from the heart, and the second is the flow of air into and out of the lungs. These two processes generate signals which can be easily differentiated from each other. The signal corresponding to the flow of blood results in a decrease in impedance at the end of every compression because blood, a low impedance fluid, is removed from the circuit, forcing current to flow through higher impedance channels. The flow of air through the lungs results in a decrease in impedance at the end of compressions because air, which does not conduct electricity, is removed from the circuit.

The two signals can be easily filtered from each other because the rate at which each process affects the impedance signal is different. In most cases, there would be little resistance to air flowing out of the lungs, whereas, in order to pump blood, the pressure in the ventricles must exceed the pressure in the arteries. This would cause a marked delay in the signal generated by blood flow in the heart and a clear threshold at which the aortic and pulmonary valves open and blood flows out of the ventricles.

The same electrodes can be used for defibrillation as well as impedance readings. However, in order to maximize the fidelity of data, it is preferable to use a tetrapolar electrode or a five to six electrode configuration for impedance recordings. These electrodes can be integrated into the existing defibrillator pads. In one embodiment, six electrodes are built into two pads, where one electrode in each pad is used for delivering the defibrillation shock, one electrode in each pad is used for delivering the current for measuring impedance and one electrode in each pad is used for recording the voltage for measuring impedance.

In another embodiment, each of the two pads has two electrodes. One electrode in each pad is used for delivering current for impedance measurements, and one electrode in each pad is used for recording voltage and measuring impedance. One or both electrodes in each pad are then used for delivering the defibrillation shock. In the five electrode embodiment, one electrode both generates and records signal. In another embodiment, each of the two pads has only a single electrode, which is used for delivering the impedance measuring current, recording voltage, and delivering the defibrillation shock.

In all embodiments, the impedance measurement circuitry is preferably protected from the defibrillation shock by protective circuitry including but not limited to, electronic switches that switch off before the defibrillation shock is delivered, fuses, circuit breakers, and switches which create protective short circuits.

In actuality, it is not depth of compression that is important, but rather the change in intrathoracic volume, which drives volume out of the heart to supply the body, brain, and the heart itself. One embodiment of the invention provides a specific measurement that is better correlated with a change in three dimensional intrathoracic volumes which is more advantageous than the current measurements along a single line of displacement. To date, devices have only been able to measure this one-dimensional sternal displacement and the recommendations have not prescribed a difference in technique to address differences associated with the size of the patient, except for pediatrics where the recommendation is for compressions to be between ⅓ and ½ the anteroposterior diameter of the chest. One embodiment of the instant device measures the change in intrathoracic volume of a given patient and provides a more appropriate metric of effectiveness of chest compressions. In one embodiment, the instant device provides a measurement based on intrathoracic volumes for feedback to rescuers to help them deliver CPR appropriate to the size and intrathoracic anatomy of a given patient.

In one embodiment, the device that measures intrathoracic volumes also, simultaneously, delivers information about ventilatory rate. In a preferred embodiment, the device delivers information about not only ventilatory rate, but ventilatory (tidal) volume as well. Tidal volume is equally important to rate in providing appropriate patient ventilation, in fact, the critical value is minute ventilation (tidal volume and respiratory rate), the actual amount of air that is exchanged in one minute. Unfortunately, tidal volume and minute ventilation are in general ignored in a patient not on a ventilator for lack of a way to measure or track volume based parameters. In one embodiment, the device provides feedback to the rescuer to make sure that ventilated breaths are totally exhaled to minimize baseline intrathoracic pressure and therefore maximize the effect of each cardiac compression.

In one embodiment, full expansion of the thorax following a compression, or "recoil" can be assessed. In one embodiment, the shape of the curve of the intrathoracic volume can be analyzed to optimize speed of delivery of the compression (not rate, but rather rapidity of the compression motion itself, and rapidity and completeness of the "letting go" or recoil phase), in one iteration, the device displays this information. In a preferred embodiment the device analyzes this information and gives audio and/or visible stimulus to optimize compressions. Similarly, in another embodiment, the shape of the curve associated with ventilator breaths can be demonstrated and feedback delivered in multiple ways. Prior to being placed on a ventilator, optimum breaths should be delivered quickly and with appropriate volume and rapidly released. In one embodiment, the device analyzes the respiratory curve and directs the caregiver to modify technique to optimize both ventilatory and cardiac interventions.

One major disadvantage of the prior methods of monitoring CPR is that the pressure sensor would produce inaccurate results if the patient's body moved during the CPR. For example, if the patient is on a soft bed, the sensor would report the force accelerating the patient's body. This force may not be compressing the chest at all, but instead merely moving the patient. Such a device is cumbersome and not easily implemented in the CPR setting. In comparison, the method described herein is not affected by the motion of the patient's body. While certain devices of the prior art use measurements of blood flow to try to determine adequacy of CPR and others use linear chest wall motion, surprisingly, it has been discovered that measurements of changes in thoracic impedance as related to impedance of air in the chest cavity and in the lungs, either with or without additional information, provides an excellent metric of adequacy of CPR.

In one embodiment, the complete intrathoracic and compression measurement system is integrated completely into the lead/impedance electrode pad. This provides the unique advantage of a low cost, light weight, and ideally situated indicators of performance of heart compression and ventilation. Many current challenges of power, electrical isolation and bulkiness of equipment would be eliminated by this integration. The unique application and environment of the emergent care setting provides unique challenges and opportunity for this low power, simple, smart electrode pad system. This unique and unexpected simple solution would provide the ideal solution for the clinician, EMS and Fire professionals. This optimal lightweight design will provide both respiratory and cardiac diagnostic indicators and also lead the emergency care provider both experienced and novice through the steps of proper diagnosis and treatment for respiratory and cardiac care.

With reference to FIG. 1, an exemplary and preferred system includes at least one general-purpose computing device 100, including a processing unit (CPU) 120, and a system bus 110 that couples various system components including the system memory such as read only memory (ROM) 140 and random access memory (RAM) 150 to the processing unit 120. Other system memory 130 may be available for use as well. The invention preferably operates on a computing device with more than one CPU 120 or on a group or cluster of computing devices networked together to provide greater processing capability. The system bus 110 may be any of several types of bus structures including a memory bus or memory controller, a peripheral bus, and a local bus using any of a variety of bus architectures. A basic input/output (BIOS) stored in ROM 140 or the like, preferably provides the basic routine that helps to transfer information between elements within the computing device 100, such as during start-up. The computing device 100 further preferably includes storage devices such as a hard disk drive 160, a magnetic disk drive, an optical disk drive, tape drive or the like. The storage device 160 is connected to the system bus 110 by a drive interface. The drives and the associated computer readable media provide nonvolatile storage of computer readable instructions, data structures, program modules and other data for the computing device 100. The basic components are known to those of skill in the art and appropriate variations are contemplated depending on the type of device, such as whether the device is a small, handheld computing device, a desktop computer, a laptop computer, a computer server, a wireless devices, web-enabled devices, or wireless phones, etc.

In some embodiments, the system is preferably controlled by a single CPU, however, in other embodiments, one or more components of the system is controlled by one or more microprocessors (MP) or other computing devices. Additionally, combinations of CPUs and MPs can be used. Preferably, the MP is an embedded microcontroller; however other devices capable of processing commands can also be used.

Although the exemplary environment described herein employs the hard disk, it should be appreciated by those skilled in the art that other types of computer readable media which can store data that are accessible by a computer, such as magnetic cassettes, flash memory cards, digital versatile disks, cartridges, random access memories (RAMs), read only memory (ROM), a cable or wireless signal containing a bit stream and the like, may also be used in the exemplary operating environment.

To enable user interaction with the computing device 100, an input device 190 represents any number of input mechanisms, such as a microphone for speech, a touch-sensitive screen for gesture or graphical input, electrical signal sensors, keyboard, mouse, motion input, speech and so forth. The device output 170 can be one or more of a number of output mechanisms known to those of skill in the art, for example, printers, monitors, lights, projectors, speakers, and plotters. In some embodiments, the output can be via a network interface, for example uploading to a website, emailing, attached to or placed within other electronic files, and sending an SMS or MMS message. In some instances, multimodal systems enable a user to provide multiple types of input to communicate with the computing device 100. The communications interface 180 generally governs and manages the user input and system output. There is no restriction on the invention operating on any particular hardware arrangement and therefore the basic features here may easily be substituted for improved hardware or firmware arrangements as they are developed.

For clarity of explanation, the illustrative system embodiment is presented as comprising individual functional blocks (including functional blocks labeled as a "processor"). The functions these blocks represent may be provided through the use of either shared or dedicated hardware, including, but not limited to, hardware capable of executing software. For example the functions of one or more processors presented in FIG. 1 may be provided by a single shared processor or multiple processors. (Use of the term "processor" should not be construed to refer exclusively to hardware capable of executing software.) Illustrative embodiments may comprise microprocessor and/or digital signal processor (DSP) hardware, read-only memory (ROM) for storing software performing the operations discussed below, and random access memory (RAM) for storing results. Very large scale integration (VLSI) hardware embodiments, as well as custom VLSI circuitry in combination with a general purpose DSP circuit, may also be provided.

Embodiments within the scope of the present invention may also include computer-readable media for carrying or having computer-executable instructions or data structures stored thereon. Such computer-readable media can be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium which can be used to carry or store desired program code in the form of computer-executable instructions or data structures. When information is transferred or provided over a network or another communications connection (either hardwired, wireless, or combination thereof) to a computer, the computer properly views the connection as a computer-readable medium. Thus, any such connection is properly termed a computer-readable medium. Combinations of the above should also be included within the scope of the computer-readable media.

Computer-executable instructions include, for example, instructions and data which cause a general purpose computer, special purpose computer, or special purpose processing device to perform a certain function or group of functions. Computer-executable instructions also include program modules that are executed by computers in stand-alone or network environments. Generally, program modules include routines, programs, objects, components, and data structures, etc. that perform particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps.

Those of skill in the art will appreciate that other embodiments of the invention may be practiced in network computing environments with many types of computer system configurations, including personal computers, hand-held devices, multi-processor systems, microprocessor-based or programmable consumer electronics, network PCs, minicomputers, mainframe computers, and the like. Networks may include the Internet, one or more Local Area Networks ("LANs"), one or more Metropolitan Area Networks ("MANs"), one or more Wide Area Networks ("WANs"), one or more Intranets, etc. Embodiments may also be practiced in distributed computing environments where tasks are performed by local and remote processing devices that are linked (either by hardwired links, wireless links, or by a combination thereof) through a communications network. In a distributed computing environment, program modules may be located in both local and remote memory storage devices.

The invention preferably comprises an impedance system for measuring intrathoracic volume with integrated electronics to convert measured impedance values to volume, impedance measuring device and a computer. The impedance measuring device comprises circuitry, at least one computing device, preferably a microprocessor and preferably four leads, where two leads are used for injecting current into the subject's body and at least two are used for reading the voltage response of said patient's body. In one embodiment, the electrodes are incorporated into defibrillator pads as described herein. In one embodiment, electrodes may be part of a system that also delivers standard EKG or ICG readings. In one embodiment electrodes may be the same as those that provide EKG input. In one embodiment, electrodes are attached horizontally to the mid-axillary line at the level of the sixth rib. However, the electrodes can be placed higher or lower on the thorax. In one embodiment multiple electrodes are used, with some incorporated into defibrillator pads and others incorporated into EKG signal leads. Furthermore, electrodes may be placed in other locations and configurations (e.g. vertically along the thorax, at an angle across the thorax, or from a position on the front of the patient to a position on the back of the patient), depending on the patient, the situation and other physiological concerns (e.g. if the patient has a pacemaker or other artificial device).

The impedance measuring device is preferably connected to a computing device that is coupled to a defibrillator device or other CPR assistance device. A digital interface is used to prevent data from corruption in transfer. In one embodiment, the interface provides protection to the system from a defibrillation shock.

In a preferred embodiment, the Transient Voltage Suppression diodes in combination with high impedance resistors are used to simultaneously protect device from ESD pulses, including high voltage pulses from defibrillator, by short-circuiting the device and to limit passing current through device to avoid interference with defibrillator's current distribution. The device data is preferably not corrupted by ESD event or defibrillator discharge and device functionality is preferably in no way impeded. In another embodiment the impedance measuring device is protected by other types of circuitry which includes at least some of the following: high impedance resistors, fuses, circuit breakers, transistors, MOSFETs, or switches.

In the preferred embodiment, the device contains circuitry and software that automatically calibrates the device. In one embodiment, calibration is aided by data acquired through bioelectrical spectral impedance analysis, a process which measures tissue impedance at various frequencies. In this embodiment, data from bioelectrical impedance analysis may be used to calculate certain characteristics of the subject including, but not limited to, hydration level, baseline impedance, and body composition. A low level of hydration causes the electrical impedance of the body to be greater. A high level of fat in the body would also cause an increase in the average electrical impedance of the body, but likely a decrease in overall impedance as electricity passes through the path of least resistance. Muscle is much more vascular than fat and contains more conductive electrolytes, so a muscular patient's body would have much lower electrical impedance than a similarly size person who was not as muscular. Scaling the calibration factor based on these inputs makes the calculations more accurate.

In one embodiment, calibration of the device of the invention is based on the metabolic requirements of body tissue. Predictions preferably involve multiplying the patient's measured, estimated body weight, or ideal body weight by a volume of air or volume of air per minute required by a unit of body weight. The ideal body weight is determined from a patient's height, race, and/or age and may further be determined with one or more of the Devine, Robinson, Hamwi, and Miller formulas.

In another embodiment, the device preferably comprises an integrated module to simulate a patient and allow for automated system testing and demonstrations. Automated system tests improve the performance of the device and ensure that it is functioning correctly before use.

In the preferred embodiment, the device utilizes an analog divider to compensate for slight deviations in the injected current and increase the accuracy of acquired data. The analog divider in the preferred embodiment would be placed after the demodulator and before the rectifier. In other embodiments the analog divider may be placed in other locations in the circuit including, but not limited to, after the precision rectifier or before the demodulator.

In the preferred embodiment, the device utilizes adaptive electronics driven by a microprocessor to maintain the appropriate gains on the different amplifiers in the circuit to prevent the signal from going out of range and maintain high S/N ratio. The microprocessor tracks the set gains at each of the hardware amplifiers and compensates appropriately during its calculations so that it always outputs an appropriate value.

Figure 2:
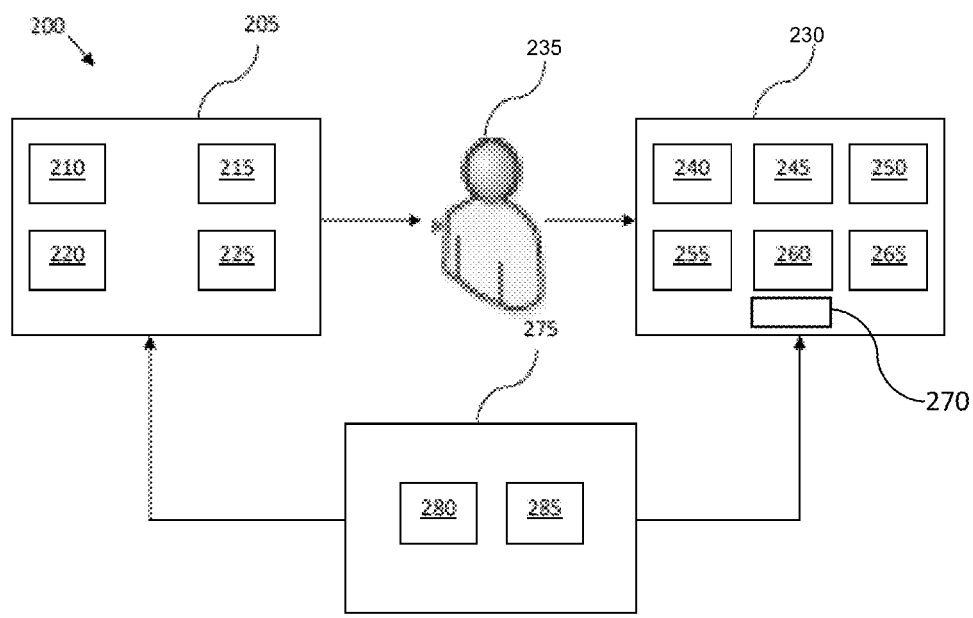
FIG. 2 illustrates one embodiment of a device of the invention.

FIG. 2 is a schematic of an embodiment of a system 200 of the invention. The electrical signal originates from signal source 205. Preferably, an adjustable function generator 210 (e.g. a XR2206 chip) is used to generate the electrical signal. The function generator 210 is preferably adjustable via a microprocessor (MP) 275 or manually. In some embodiments, the function generator can be tuned in order to improve the signal. Tuning can occur once or multiple times. Bio-impedance spectroscopy can be used to detect levels of hydration at different frequencies, which can be used to calibrate function generator 210. Similarly, body fat percentages can be calculated.

Signal source 205 also comprises a current generator 215 (e.g. a Howland circuit). Current generator 215 preferably keeps the source current constant despite changes in pad contact (unless the contact is totally broken). In the preferred embodiment, current generator 215 can be tuned to improve performance, which can be done manually or automatically by the MP 275. In preferred embodiments, the pad contact quality is monitored and a warning is produced when the pad contact is broken or too poor quality for the electronics to compensate. Signal source 205 may also comprise a current monitor 220 to calculate impedance.

In a preferred embodiment, signal source 205 also comprises a patient simulator 225. Patient simulator 225 can simulate changes in the impedance with parameters similar to a real patient. Patient simulator 225 can be used for testing system 200 as well as calibration of the circuitry.

The signal from signal source 205 passes through patient 235 and is received by sensor 230. Preferably, sensor 230 comprises an input impedance amplifier 240. Impedance amplifier 240 suppresses the effect of poor or variable pad contact on measurement. The gain of impedance amplifier 240 is preferably controlled by the MP 275 to provide an enhanced signal to the other modules. Sensor 230 preferably also comprises a signal filter 245 to remove interference from the power grid, etc. Signal filter 245 may be a standard high-pass filter, a demodulator, or another signal filter. Synchronous demodulators are often used for detecting bio-impedance changes and stripping out motion artifacts in the signal.

In a preferred embodiment, the signal is split into two paths. The first path preferably demodulates the measured signal using the generator signal as a carrier. The second path preferably uses a 90-degree phase rotating circuitry before demodulation. Both demodulated signals can be converted into RMS values using voltage-to-RMS converters. Measured separately, the signals are summed and then the square root is calculated. This allows for compensation for any phase shift in the subject and for separate measurements of resistance and reactance, which provides valuable information for motion artifact compensation as well as hydration levels, fat percentages, and calibration coefficient calculations.

Additionally, sensor 230 may comprise an analog divider 250, which divides the measured voltage signal by the signal from the current monitoring circuit to calculate impedance. Sensor 230 preferably also comprises a precision rectifier or root mean square to direct current (RMS-to-DC) chip 255 with a low pass filter to remove the carrier frequency. The output of sensor 230 is preferably a DC signal proportional to the patient's impedance. Sensor 230 may also comprise a band-pass filter 260 to select only the respiratory rates by filtering out the portion of the signal not corresponding to the respiration. Band-pass filter 260 may be calibrated manually or automatically by the MP 275. Preferably, sensor 230 comprises a multiplexor 265 controlled by the MP 275 to accommodate multiple probe pairs. Preferably there are 2 probe pairs, however more or fewer probe pairs are contemplated. Sensor 230 may also comprise an output amplifier 270. Output amplifier 270 is preferably controlled by the MP 275 and provides a signal to an analog-to-digital converter (ADC) 280 for high precision digitization. Oversampling is used to reduce measurement noise which may originate from different sources (e.g., thermal, electronic, biological, or EM interference). MP 275 commands ADC to take measurements with as high a cadence as possible and then averages the obtained data over the time intervals corresponding to the sampling frequency. The sampling frequency is the frequency of the impedance sampling as it is presented to the computer by the impedance measuring device. The frequency is preferably set sufficiently high to monitor all the minute features of respiration.

Using controllable gains and oversampling preferably allows the system to measure the impedance with extremely high effective precision (estimated 28-bit for current implementation, or 4 parts per billion).

Both signal source 205 and sensor 230 are controlled by MP 275. MP 275 preferably comprises at least one ADC 280 monitoring the signal processing, and at least one digital output 285 to control the digital potentiometers, multiplexors, op-amps, signal generator, and other devices. Preferably, MP 275 communicates with an interface device (e.g. a tablet PC, laptop, netbook, cell phone or other portable computing device) using a wired (e.g. USB, serial) or wireless (e.g. Bluetooth or wireless internet) connection. Preferably, the interface device would display feedback to the CPR technician. Preferably the interface would display one or more of the following metrics: tidal volume, respiratory rate, minute volume, compression depth, and compression rate.

Figure 3:
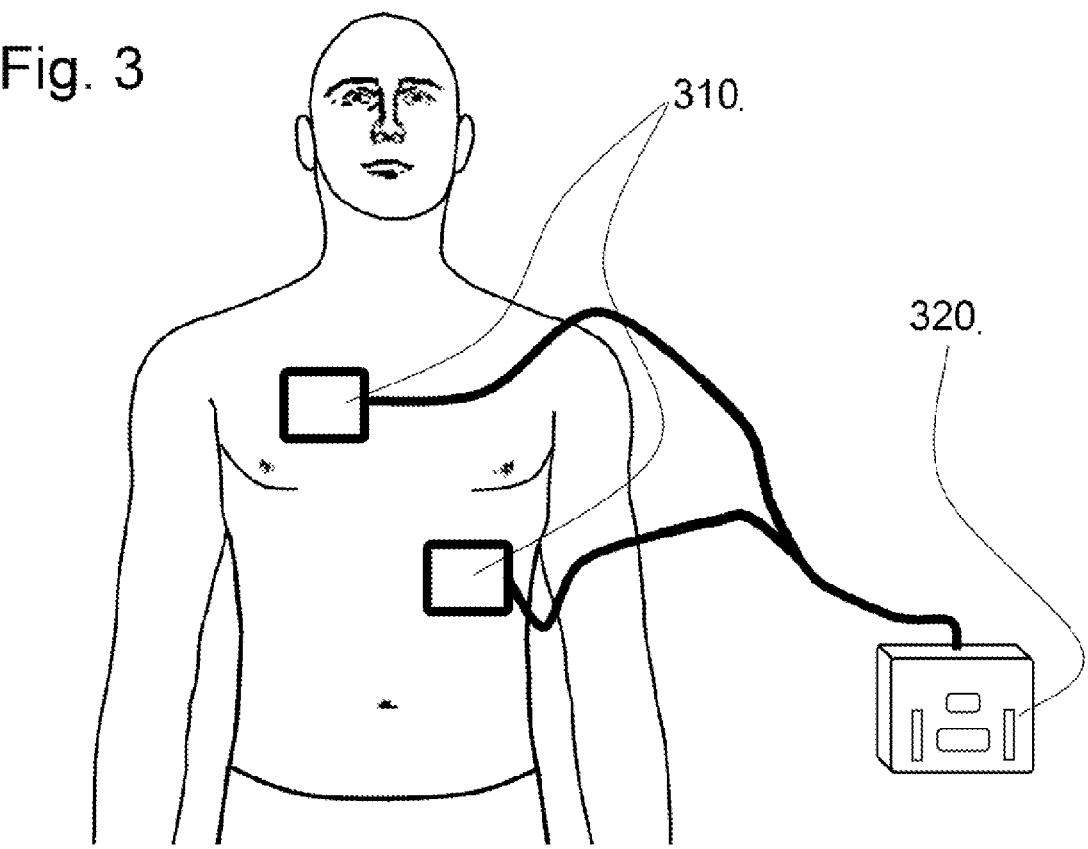
FIG. 3 shows an embodiment of a device of the invention in use on a patient.

FIG. 3 shows an embodiment of the invention in use during a CPR session. Leads 310 are placed on the patient's chest to measure thoracic impedance. The device 320 is beside the patient. The device interprets thoracic impedance and provides feedback to the CPR operator in audio, visual and/or textual format.

Figure 4:
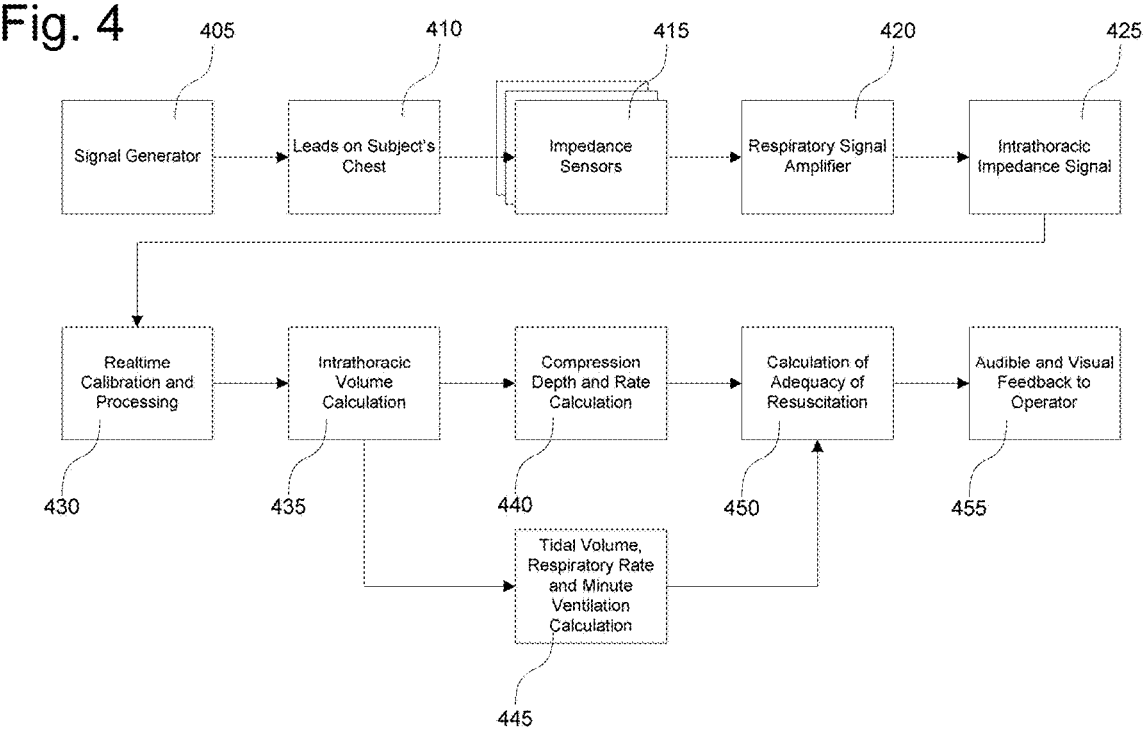
FIG. 4 illustrates the flow of current and information through the different parts of a device representing an embodiment of the invention.

FIG. 4 shows the flow of electric current and data signal through an embodiment of the invention. A signal generator 405 inside the device injects current across the patient's chest through the leads 410. Impedance sensors 415 in the leads measure the thoracic impedance and respiratory signal is amplified 420. The device then converts the analog intrathoracic impedance signal to a digital signal 425 to be used for calibration and processing 430. The patient's intrathoracic volume is then calculated 435, and split into its pulmonary 445 and cardio components 440. The device then determines whether the resuscitation is adequate 450, and what feedback could improve the quality of resuscitation. Appropriate audio and/or visual feedback is administered through the user interface 455.

Figure 5:
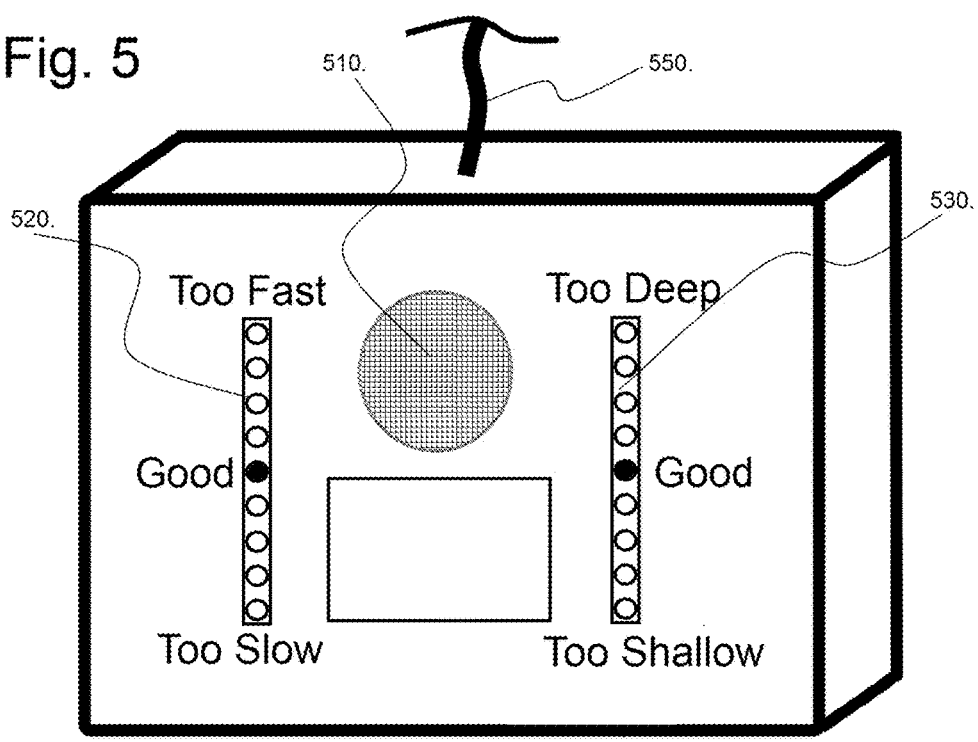
FIG. 5 illustrates an embodiment of the user interface of the invention.

FIG. 5 shows a possible embodiment of the user interface of the invention. The device is connected to the leads 550 which measure thoracic impedance of the subject. The device monitors the quality of the CPR and gives feedback to the operator. The device can give audio feedback through the speaker 510 to tell the operator to change the speed or the depth of chest compressions. The device can also show the operator which adjustments should be made using LED indicators. The compression speed indicator 520 alerts the operator if an adjustment in timing of compressions is necessary. The compression depth indicator 530 alerts the operator if an adjustment in compression depth is necessary. Both LED indicators are able to show the degree to which CPR performance is off from the ideal case by lighting further away from the "Good" LED.

Figure 6:
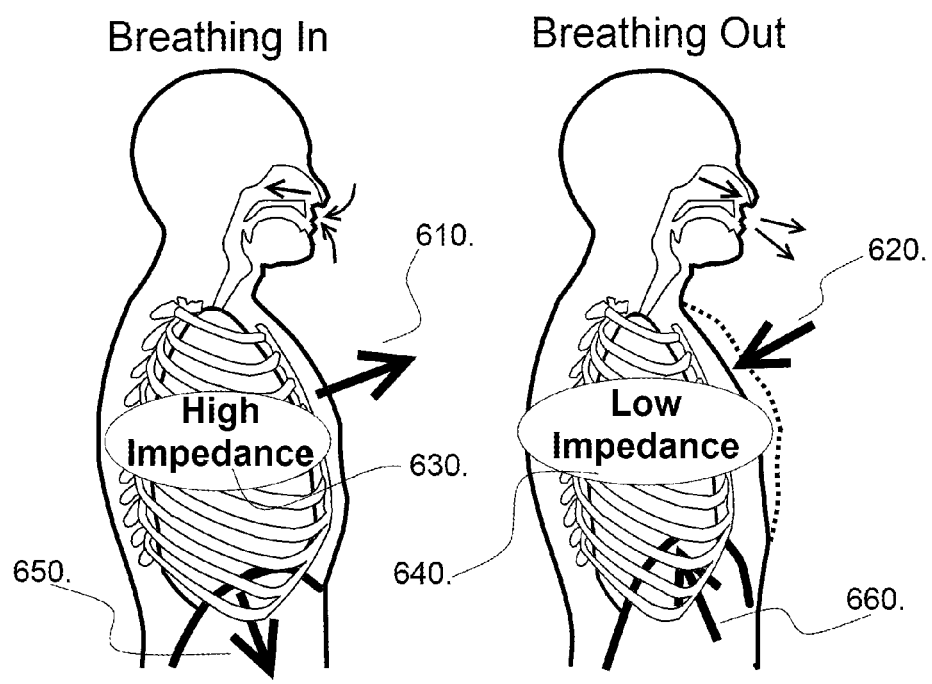
FIG. 6 shows the relative levels of thoracic impedance related to the volume of inhaled air.

FIG. 6 shows how thoracic impedance is used to calculate ventilation volume. When the patient breathes in, the diaphragm contracts 650 and the chest expands 610. With more air inside the lungs, the impedance across the thorax increases 630. Conversely, when the patient breathes out, the diaphragm relaxes 660 and the chest wall contracts 620. There is less air inside the chest and impedance across the thorax decreases 640.

Determining the adequacy of compression is better related to a change in intrathoracic volume than displacement of the sternum. Simple sternal displacement is not a good determinant of the adequacy of compression because it does not take into account movement of the entire patient. For example, an accelerometer could read large displacement if the patient were on a soft bed and the entire patient moved two inches. In this case the system would register a proper the displacement and the instructions the system provided would lead to a situation where inadequate CPR was being performed. Sternal displacement also does not take into account differences in patient size, weight or body habitus. A 2 inch displacement on a thin, 20 year old, 5 foot, 100 lb female has a very different effect than that on a 50 year old, 6 foot, 300 lb male.

Within emergency situations, first responders require not only an automated external defibrillator, but also a device that can assist during cardiopulmonary resuscitation (CPR) to determine whether a "shock" is required. The invention described herein is able to provide a superior, more clinically useful, and easier to use method for assuring adequacy of chest compressions. The novel solution reports changes in intrathoracic volume (lung volume) which more accurately reflect the adequacy of CPR. The invention preferably provides near real-time, objective measurement and corrective feedback on compression and ventilation to encourage CPR performance by skilled or unskilled rescuers in accordance with established guidelines. In one embodiment, the information from the invention will provide input for algorithms that direct caregiver actions such as delivering a "shock", increasing or decreasing the depth of compressions, increasing or decreasing the rate of compression, increasing or decreasing the rate of ventilation, increasing or decreasing the volume of ventilation.

In one embodiment, the measurement is related to the predicted intrathoracic volume for a given patient's parameters. In another embodiment the measurement is corrected for patient size by placement of the electrodes. In a preferred embodiment, the intrathoracic volume is calculated from an impedance measurement. In another embodiment, sternal displacement is calculated from impedance data. In another embodiment, intrathoracic volume is calculated from a set of accelerometers (actually used to calculate intrathoracic volume and volume changes and different from those used to measure simple sternal displacement). In another embodiment, intrathoracic volume is calculated from combination of intrathoracic volume with existing accelerometer technology with unilateral or other displacements provided from the accelerometers.

In one embodiment, the impedance or accelerometer based measurements of intrathoracic volume and change in intrathoracic volume also provide a rate of compression. In one embodiment, the impedance or accelerometer based measurements of intrathoracic volume and change in intrathoracic volume provide input to an algorithm which controls a device to command or comment to the rescuer to improve CPR or affirm its adequacy. The commands include, for example, compress harder, compress softer, modify compression depth, compress faster, compress slower, good speed of compression, modify ventilation volume, modify speed with which a ventilation is delivered (give a shorter breath, give a longer breath), ventilate faster, ventilate slower, and good speed of ventilation. In another embodiment the invention provides an audio signal, visual signal or textual signal. In one embodiment, the invention gives a cue for initiating each compression. In one embodiment the invention gives a cue for initiating each ventilation.

In one embodiment, impedance or accelerometer based measurements of intrathoracic volume and change in intrathoracic volume then provide input to an algorithm which controls an automatic CPR compression device which is an open or closed loop system. In one embodiment, impedance or accelerometer based measurements of intrathoracic volume and change in intrathoracic volume then provide input to an algorithm which controls an automatic ventilation device which is an open or closed loop system. In one embodiment, impedance or accelerometer based measurements of intrathoracic volume and change in intrathoracic volume then provide input to an algorithm which controls an automatic combined CPR compression and ventilation device which is an open or closed loop system.

In one embodiment, the invention reports adequacy of ventilation and provides instruction for improvement for a hand-bagged patient or a closed loop system back to a transport ventilator. In one embodiment, the invention reports both the adequacy of ventilation and compressions and provides instruction for improvement or integrates with other equipment for closed loop control One product on the market, The Phillips Q-CPR meter, provides a real-time CPR measurement and feedback tool to provide objective measurement and real-time corrective feedback on both the compression and ventilation components of CPR which is available in both manual defibrillation and AED modes. The Q-CPR device provides information about compression depth and rate as well as ventilation rate to encourage caregivers to perform CPR on adults in accordance with AHA/ILCOR guidelines, but does not provide information as to intrathoracic or lung volumes. One embodiment of the instant invention adds the capability to measure respiratory volume to the respiratory rate measurements provided by other technologies. One embodiment of the instant invention adds increased utility of a measurement of intrathoracic volume instead of or in addition to compression depth for adequacy of resuscitation. One embodiment of the instant invention adds information about cardiac flow/output derived from cardiac impedance data to the set of information.

Another product in the marketplace, the Phillips HeartStart MRx measures ventilation through defibrillation pads by detecting changes in thoracic impedance. The ventilation rate is presented as ventilations-per-minute (vpm). The Phillips system does not have the capability to measure intrathoracic volumes as it relates to ventilatory volumes or intrathoracic volume changes associated with compressions. It is a novelty of the instant invention that the impedance signal is collected and processed so that specific information as to intrathoracic volumes can be utilized to better direct compressions and ventilation during CPR.

In one embodiment, impedance electrodes (preferably four) are included in the defibrillator pads of a transport monitor/defibrillator. In another embodiment, impedance electrodes (preferably four) are placed separate from defibrillator pads in anatomically relevant locations to record intrathoracic volume changes. Preferably, the EKG signal is obtained from the four impedance electrodes so that additional leads do not need to be placed. Preferably, the impedance device is shielded from a defibrillator shock.

The invention can preferably be used for any patient requiring CPR or evaluation for the necessity of CPR. In one embodiment, the device will be ruggedized for use within emergency transport for EMTs and military personnel. One embodiment of the invention assists the caregiver in providing appropriate management of timing and performance and coordination of compressions and delivery of breaths (ventilation) by barrier device, mask or endotracheal tube.

One embodiment includes a CPR feedback device that can assist an emergency technician or military medic with specific instructions and corrections regarding CPR compressions to improve outcomes. In one embodiment, the invention utilizes leads associated with a typical AED. The EMT would attach the leads integrated into existing defibrillator pads and/or EKG leads prior to compression. Changes in impedance are detected by generating an alternating or constant current through the thorax. Changes in impedance are related to the rate at which the chest is being compressed, as well as the depth of each compression. The measured compression rate is compared with optimal values and may be enforced through an alarm system, where the rescuer is notified if the compression rate is either too high or too low or appropriate. The alarm can be audible, visual, or a combination thereof. The measured compression depth is compared with optimal values and enforced through an alarm system, where the administrator of compressions is notified if the compression depth is either too high or too low or adequate.

One embodiment of the device combines the impedance of another intrathoracic volume measuring device and delivers the data with other information derived from another device or recording method, including but not limited to, written log, defibrillator, cardiac monitor, respiratory monitor, end tidal CO2 (ETCO2) monitor, pulse oximeter, ventilator and either stores these data or presents a reduction set of the data to the caregiver in near-real time to assist with ongoing CPR.

One embodiment is used for quality improvement as part of the development process for mechanical devices to deliver CPR most effectively. Another embodiment is to provide ongoing quality improvement in the field to caregivers while they are performing CPR. Another embodiment is to provide data for debriefing after a CPR event for quality improvement by storing the data from the impedance or other intrathoracic volume measuring device and delivering the data with other information derived from any other device or recording method including but not limited to written log, defibrillator, cardiac monitor, respiratory monitor, ETCO2 monitor, pulse oximeter, ventilator. In one embodiment separate leads are used to stimulate and monitor impedance. In one embodiment, EKG leads are used to stimulate and monitor impedance. In one embodiment, defibrillator pads are used to stimulate and monitor impedance.

In one embodiment the invention provides assessment of patients breathing parameters including respiratory rate, tidal volume and minute ventilation (which can be reported on a screen or via a voice/auditory component or other method), advising a care giver on adequacy of respiration whether spontaneous breathing or provided by hand bagging or transport or other ventilator. One embodiment provides information so that an inexperienced rescuer can be instructed to deliver CPR according to guidelines.

One embodiment provides information with a variable amount of detail so that BLS and ALS level caregivers and non-medical personnel can optimize their CPR delivery. In one embodiment, the invention provides feedback to the rescuer regarding compression rate, depth, and complete release, as well as no compression activity (or "hands-off" time), and ventilation rate.

In one embodiment, the invention provides open or closed feedback to an automatic compression device regarding one or more of the following: compression rate, depth, and complete release, as well as no compression activity (or "hands-off" time), ventilation rate.

In one embodiment, the invention provides open or closed feedback to an integrated system that performs both ventilation and automatic compressions regarding one or more of the following: compression rate, depth, and complete release, as well as no compression activity (or "hands-off" time), and ventilation rate.

In one embodiment, the invention provides open or closed feedback to a ventilator regarding one or more of the following: compression rate, depth, and complete release, as well as no compression activity (or "hands-off" time), and ventilation rate.

One embodiment provides assessment of adequacy of chest compression (which can be reported on a screen or via a voice/auditory component or other method) by measuring changes in impedance related to intrathoracic lung volume.

One embodiment provides assessment of actual or relative cardiac flow/output based on impedance measurements (which can be reported on a screen or via a voice/auditory component or other method). This can be measured and reported independently, or can be integrated with thoracic volume data to define adequacy of CPR compressions. In one embodiment, the device reports absolute values or trend measurements (which can be reported on a screen or via a voice/auditory component or other method). In one embodiment, the device stores results for later review.

Mechanical CPR is still not included in the American Heart Association guidelines. One embodiment of the invention provides feedback to a mechanical CPR device to optimize its delivery of compressions.

Mechanical devices can operate at a single baseline level, or can be adjusted initially, intermittently or in real time, based on feedback from a device that detects and reports adequacy of compression and/or ventilation. This adjustment can be performed by the caregiver (open loop control) or by the mechanical device itself (closed loop control).

One of the drawbacks of current mechanical CPR is that there is not adequate feedback of changes in intrathoracic volumes to optimize its implementation. One embodiment of the invention includes an integrated device that can provide ongoing audio feedback for both compressions and ventilation that would optimize CPR performance.

Patients with an abnormal state of hydration pose an additional problem to impedance cardiography by changing the baseline impedance, which is why it is important to combine impedance cardiography with impedance pneumography.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. Additionally, U.S. Provisional Application Nos. 61/449,811 and 61/480,105 are specifically and entirely incorporated by reference herein. It is intended that the specification and examples be considered exemplary only with the true scope and spirit of the invention indicated by the following claims. Furthermore, the term "comprising" includes the terms "consisting of" and "consisting essentially of," and the terms comprising, including, and containing are not intended to be limiting.

The invention claimed is:

1. A device for determining adequacy of Cardiopulmonary Resuscitation (CPR), comprising:
    an electrical current source generator;
    an electrical voltage sensor sensing current generated by the electrical current source generator;
    a microprocessor, wherein the microprocessor determines changes in impedance of a patient based on the current sensed by the electrical voltage sensor;
    non-transitory computer readable media with instructions executing on the microprocessor, wherein the non-transitory computer readable media executed:
        determines change in total intrathoracic volume of the patient, which includes lung volume and cardiac volume, based on the changes in impedance of the patient;
        determines an adequacy of rate of compression and depth of compression based on the change in total intrathoracic volume of the patient; and
        outputs a signal indicating the adequacy of the rate of compression and depth of compression; and
    at least one feedback component, wherein the feedback component is an indicator and the feedback component provides instructions to a CPR operator to adjust at least one of speed of chest compression and depth of chest compression based on the outputted signal.

2. The device of claim 1, wherein the electrical current source generator is comprised of at least one of a function generator, a current generator, and a current monitor.

3. The device of claim 1, wherein the electrical voltage sensor comprises at least one of an input amplifier, a signal filter, an analog divider, a rectifier, a root mean square to direct current (RMS-to-DC) chip, a band-pass filter, a multiplexor, and an output amplifier.

4. The device of claim 3, comprising two demodulators, wherein the first demodulator filters an impedance signal with a generator signal as a carrier and the second demodulator filters the impedance signal with 90-degree phase rotating circuitry.

5. The device of claim 1, further comprising at least one of ventilator, an automatic compression device, and a defibrillator.

6. The device of claim 5, wherein the signal is a closed feedback that directs at least one of the ventilator to adjust ventilation rate, the automatic compression device to adjust at least one of compression rate, depth of compression, complete release, and no compression activity.

7. The device of claim 5, wherein the non-transitory computer readable media further directs timing of defibrillation.

8. The device of claim 5, further comprising leads adapted to couple the patient to the electrical current source generator and the electrical voltage sensor.

9. The device of claim 8, wherein the leads are coupled to paddles of the defibrillator.

10. The device of claim 9, further comprising protective circuitry to protect each electronic element of the device from a shock generated by the defibrillator.

11. The device of claim 1, wherein the non-transitory computer readable media additionally: calculates respiration volume and respiration rate based on the change in total intrathoracic volume of the patient; and
    outputs a second signal indicating adequacy of respiration based on the calculated respiration volume and respiration rate.

12. The device of claim 1, wherein the non-transitory computer readable media additionally: calculates respiration volume and respiration rate based on the change in total intrathoracic volume of the patient; and
    outputs a second signal indicating adequacy of ventilation based on the calculated respiration volume and respiration rate.

13. The device of claim 12, wherein the at least one feedback component further provides instructions to the CPR operator to adjust at least one of speed of ventilation and depth of ventilation based on the outputted second signal.

14. The device of claim 1, wherein the indicator is at least one of a speaker and a plurality of lights.

15. The device of claim 1, wherein the change in total intrathoracic volume corresponds to at least one of air flow and blood flow through the patient.

16. A method of determining adequacy of Cardiopulmonary Resuscitation (CPR), comprising:
    generating an electrical current at an electrical current generator;
    passing the electrical current through a patient;
    receiving the electrical current at an electrical voltage sensor after the electrical current passed through the patient;
    measuring changes in impedance levels of the patient based on the received electrical current at one or multiple frequencies;
    determining change in total intrathoracic volume of the patient, which includes lung volume and cardiac volume, based on the changes in impedance levels of the patient;

determining an adequacy of rate of compression and depth of compression based on the change in total intrathoracic volume of the patient;

outputting a signal indicating the adequacy of the rate of compression and depth of compression; and providing instructions to a CPR operator via a feedback component, wherein the feedback component is an indicator and the instructions are to adjust at least one of speed of chest compression and depth of chest compression based on the outputted signal.

17. The method of claim 16, wherein the electrical current generator is comprised of at least one of a function generator, a current generator, and a current monitor.

18. The method of claim 16, wherein the electrical voltage sensor comprises at least one of an input amplifier, a signal filter, an analog divider, a rectifier, a root mean square to direct current (RMS-to-DC) chip, a band-pass filter, a multiplexor, and an output amplifier.

19. The method of claim 16, comprising two demodulators, wherein the first demodulator filters an impedance signal with a generator signal as a carrier and the second demodulator filters the impedance signal with 90-degree phase rotating circuitry.

20. The method of claim 16, further comprising controlling at least one of a ventilator, an automatic compression device, and a defibrillator.

21. The method of claim 20, further comprising at least one of ventilator, an automatic compression device, and a defibrillator.

22. The method of claim 20, wherein the signal is a closed feedback that directs at least one of the ventilator to adjust ventilation rate, the automatic compression device to adjust at least one of compression rate, depth of compression, complete release, and no compression activity.

23. The method of claim 22, further comprising coupling leads to the patient, the electrical current generator, and the electrical voltage sensor.

24. The method of claim 23, further comprising coupling the leads to paddles of the defibrillator.

25. The method of claim 24, further comprising protecting each electronic element from a shock generated by the defibrillator with protective circuitry.

26. The method of claim 16, further comprising calculating respiration volume and respiration rate based on the change in total intrathoracic volume of the patient; and outputting a second signal indicating adequacy of respiration based on the calculated respiration volume and respiration rate.

27. The method of claim 16, further comprising calculating respiration volume and respiration rate based on the change in total intrathoracic volume of the patient; and outputting a second signal indicating adequacy of ventilation based on the calculated respiration volume and respiration rate.

28. The method of claim 27, wherein providing instructions to the CPR operator further comprises providing instructions to the CPR operator to adjust at least one of speed of ventilation and depth of ventilation based on the outputted second signal.

29. The method of claim 16, wherein the indicator is at least one of a speaker and a plurality of lights.

30. The method of claim 16, wherein the change in total intrathoracic volume corresponds to at least one of air flow and blood flow through the patient.

31. A non-transitory computer-readable media containing program instructions for determining adequacy of Cardiopulmonary Resuscitation (CPR), that causes a computer to:

generate an electrical current at an electrical current generator;

inject the electrical current into a patient via the electrical current generator;

receive the electrical current at an electrical voltage sensor after the electrical current passes through the patient;

measure change in the impedance level of the patient based on the received electrical current;

determine change in total intrathoracic volume of the patient, which includes lung volume and cardiac volume, based on the changes in impedance of the patient;

determine an adequacy of rate of compression and depth of compression based on the change in total intrathoracic volume of the patient;

output a signal indicating the adequacy of the rate of compression and depth of compression; and provide CPR instructions to a CPR operator via a feedback component, wherein the feedback component is an indicator and the CPR instructions are to at least one of adjust speed of chest compression and depth of chest compression, based on the outputted signal.

32. The media of claim 31, wherein the electrical current generator is comprised of at least one of a function generator, a current generator, and a current monitor.

33. The media of claim 31, wherein the electrical voltage sensor comprises at least one of an input amplifier, a signal filter, an analog divider, a rectifier, a root mean square to direct current (RMS-to-DC) chip, a band-pass filter, a multiplexor, and an output amplifier.

34. The media of claim 33, wherein the media further causes the computer to filter an impedance signal with a generator signal as a carrier through a first demodulator and to filter the impedance signal with 90-degree phase rotating circuitry through a second demodulator.

35. The media of claim 31, wherein the non-transitory computer readable medium includes instructions to control at least one of a ventilator, an automatic compression device, and a defibrillator.

36. The media of claim 35, wherein the media further directs at least one of the ventilator to adjust ventilation rate, the automatic compression device to adjust at least one of compression rate, depth of compression, complete release, and no compression activity.

37. The media of claim 31, wherein the media further causes the computer to:

calculate respiration volume and respiration rate based on the change in total intrathoracic volume of the patient; and output a second signal indicating adequacy of respiration based on the calculated respiration volume and respiration rate.

38. The media of claim 31, wherein the media further causes the computer to:

calculate respiration volume and respiration rate based on the change in total intrathoracic volume of the patient; and output a second signal indicating adequacy of ventilation based on the calculated respiration volume and respiration rate.

39. The media of claim 38, wherein the media further causes the computer to:

provide instructions to the CPR operator to adjust at least one of speed of ventilation and depth of ventilation based on the outputted second signal.

40. The media of claim 31, wherein the indicator is at least one of a speaker and a plurality of lights.

41. The media of claim 31, wherein the change in total intrathoracic volume corresponds to at least one of air flow and blood flow through the patient.

* * * * *